(12) United States Patent
Jones et al.

(10) Patent No.: US 7,072,036 B2
(45) Date of Patent: Jul. 4, 2006

(54) FLUORESCENCE REFERENCE PLATE

(75) Inventors: Christopher Nicholas Jones, Cardiff (GB); Philip John Meyler, Cardiff (GB); Robert Arnold Jessop, Cardiff (GB); Malcolm John Hatcher, Cardiff (GB); Michael Keith Page, Cardiff (GB); Michael Roger Looker, Cardiff (GB)

(73) Assignee: GE Healthcare UK Limited, Amersham (GB)

( * ) Notice: Subject to any disclaimer, the term of this patent is extended or adjusted under 35 U.S.C. 154(b) by 345 days.

(21) Appl. No.: 10/442,776

(22) Filed: May 21, 2003

(65) Prior Publication Data

US 2004/0036868 A1    Feb. 26, 2004

(30) Foreign Application Priority Data

Aug. 21, 2002   (GB)   ................... 0219457.9

(51) Int. Cl.
*G01N 21/01* (2006.01)
*G01N 1/10* (2006.01)

(52) U.S. Cl. ...................... 356/246; 422/102; 436/172; 356/244

(58) Field of Classification Search ................ 356/246, 356/243.1, 243.4, 244, 234.1; 422/102, 82.02, 422/942; 436/172, 164; 435/288.4
See application file for complete search history.

(56) References Cited

U.S. PATENT DOCUMENTS

| | | | |
|---|---|---|---|
| 6,171,780 B1 * | 1/2001 | Pham et al. .................... 435/4 |
| 6,187,267 B1 * | 2/2001 | Taylor et al. .................. 422/52 |
| 6,348,965 B1 * | 2/2002 | Palladino et al. ........ 356/243.1 |
| 6,607,701 B1 * | 8/2003 | Jansson et al. ............. 422/102 |
| 6,620,625 B1 * | 9/2003 | Wolk et al. .................. 436/180 |
| 6,676,734 B1 * | 1/2004 | Nagashima et al. ..... 106/31.32 |
| 2003/0012702 A1 * | 1/2003 | Hudson ....................... 422/102 |

* cited by examiner

*Primary Examiner*—Layla G. Lauchman
(74) *Attorney, Agent, or Firm*—Yonggang Ji

(57) ABSTRACT

A multi-modality fluorescence reference plate comprising wells coated with a fluorogenic compound is described, together with a method of producing such a plate. The plate has utility for calibrating fluorescent plate readers and imaging systems for measuring steady-state fluorescence, time-resolved fluorescence, fluorescence lifetime and/or fluorescence polarisation.

16 Claims, 6 Drawing Sheets

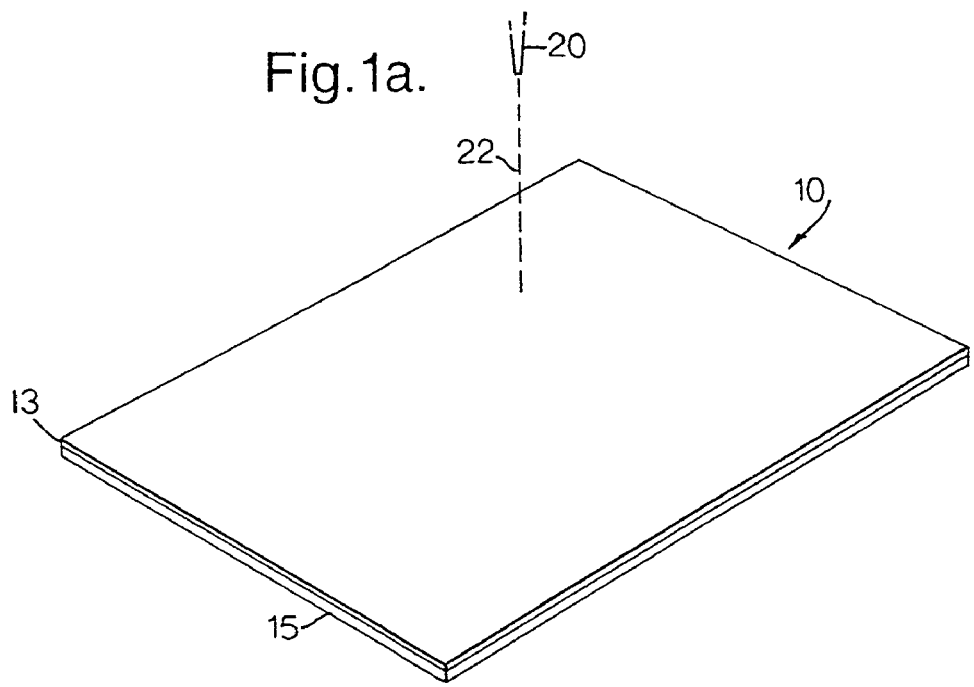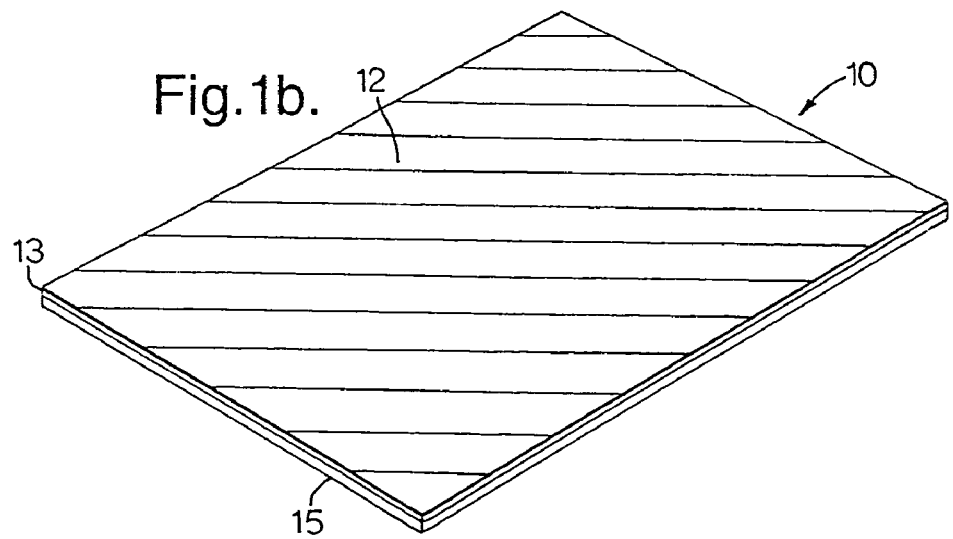

FLUORESCENCE REFERENCE PLATE

BACKGROUND OF THE INVENTION

The present invention relates to a multi-modality fluorescence reference plate useful for calibrating and testing fluorescence spectroscopic instruments, such as microscopes, imaging devices and plate readers. The invention also relates to a method of manufacturing such plates and to the use of the plates in steady-state fluorescence, time-resolved fluorescence, fluorescence polarisation and fluorescence lifetime.

Many dye molecules, when irradiated with visible or ultraviolet light, emit a portion of the absorbed energy as fluorescent light at longer wavelength. These dye molecules, known as fluorogenic compounds, are widely used in biological assays, where the fluorescent signals they produce can provide information about the system under study. The technique of fluorometry is extremely powerful, since it provides an extremely sensitive measurement on very small quantities of materials under study.

Fluorometers have three principal components: i) a light source for excitation; ii) one or more filters and/or dispersive monochromators for selecting the wavelength of interest; and iii) a detector for converting the fluorescence light into an electrical signal. Traditionally, most detectors have consisted of either a diode or a photomultiplier tube (PMT), both of which measure a single sample at a time. More recently, detectors which comprise a charge-coupled device (CCD) have been used since they enable simultaneous imaging and quantification of many fluorescent samples at one time.

The high sensitivity of fluorometric techniques, and concomitant low sample demands, has made them a favoured screening method for new drug discovery in the pharmaceutical industry where they have found great utility in high throughput screening (HTS). Multi-well or micro-well plates are frequently used in HTS since their compact format (typically 96 or 384 wells in a 126×84 mm footprint) maximises throughput while minimising sample and space requirements. Such plates are well known in the art and are available from a number of commercial suppliers (e.g. Greiner Labortechnik).

The most common form of fluorometers used in HTS are PMT-based scanners, in which one well is measured at a time in a supposedly 'identical' manner (e.g. Farcyte™, Amersham Biosciences, Buckinghamshire, UK). Fluorometers of this type are known as plate readers. The process generally involves the plate moving between readings to allow each well to be aligned beneath the detector and the fluorescent signal to be measured from each. Frequent checks are therefore necessary, using standard solutions of 'known' fluorescence, to ensure that the system is behaving correctly and that signals from all the wells are being measured in an identical manner.

More recently CCD-based imaging systems, such as Leadseeker™ (Amersham Biosciences) and Viewlux™ (PerkinElmer Life Sciences, Inc., Massachusetts, USA), have been used in HTS applications as they significantly reduce assay time and increase throughput by imaging whole plates simultaneously. The INCell™ 1000 and 3000 Cell Analysers (Amersham Biosciences) are integrated automatic image acquisition and analysis instruments for use in high throughput cell screening assays at the subcellular level. Once again, frequent checks are necessary to calibrate the instrument and ensure that it is performing in a reproducible and accurate manner.

There is therefore a continuing need for calibrating fluorometric instruments by making regular measurements on fluorescent standards. Such standards are based upon properly characterised sources of signals which do not vary significantly from test-to-test or from laboratory-to-laboratory.

Many methods exist in the art for achieving this goal. Thus, for example, Model & Burkhardt (Cytometry, 2001, 44, 309–316) report on a method for normalising fluorescent images to that of an image of a reference standard using stock solutions of fluorescein and microscope slides. This method, however, is not readily applicable to HTS and the use of micro-well plates.

U.S. Pat. No. 6,348,965 discloses a solid state device for the calibration of microplate fluorescence and absorption readers. The invention described consists of a series of optical glass probes coated with a fluorogenic material which are shaped to fit into the wells of a microplate. The user is therefore required to place the appropriate probe, coated with a particular concentration of a fluorogenic compound, manually into specific wells of the microplate. Such an operation can be both time-consuming and prone to errors. Furthermore, the continued handling of the probes can lead to excessive wear of the fluorogenic coating with a resultant reduction in fluorescent signal.

US 2002/0048817 describes standards for calibrating fluorescent instruments which consist of viscosity changing polymers and dyes. The standards can be used to dissolve a wide range of different dyes which are then subsequently dispensed into microwell plates, transformed into gels and used to calibrate the instrument. Once again, this method necessitates manual or mechanical preparation of the solutions and dispensing into micro-well plates.

US 2003/0012702 discloses a fluorescence validation microplate for testing the validity of a fluorometer. Fluorophores of known excitation and emission wavelengths are fitted or placed in the wells of the microplate. The fluorophore can be an organic or inorganic material on the surface of a film, coated or frosted onto a rigid slide, or embedded in a polymer matrix which is inserted into the wells or troughs in the plate. The preparation of such plates can be time-consuming to ensure that the fluorophore is fitted evenly into the well or trough.

Several products are commercially available for calibration of fluorometric devices. In the simplest form, Varian Inc. (Mesa Components, California, USA) provide a fluorescence reference set consisting of fluorescence standard materials in polymer blocks (ref. 66 100 103 00) for use with fluorometric instruments. Starna (Optiglass Ltd., Essex, UK) offer a similar 'Reference Set' (ref. 6BF) of stable fluorescent materials in hydrocarbon blocks. Such materials do not lend themselves readily for calibrating PMT fluorimeters and CCD-based imaging systems.

BMG Labtechnologies Ltd. (Buckinghamshire, UK) offer a 'Calibration Microplate' (ref. CLS96M) which can be used to measure fluorescence. The microplate relies on LED/solid state technology, in twelve wells, to generate a reproducible light signal in the 500–520 nm range. With only twelve wells capable of generating a signal, the calibration microplate has little utility as a reference standard for CCD-based imaging systems.

The QC Pak™ micro-well plate, supplied by Innovative Instruments Inc. (North Carolina, USA), is suitable for both PMT-based and CCD-based imaging systems. The QC Pak™ product consists of organic fluorophores (e.g. fluorescein, rhodamine, umbeliferon) embedded within a styrene matrix in the wells of an anodised aluminium 96 micro well plate. The plate is ready for use and contains a range of different fluorophores at varying concentrations, thus enabling calibration of both wavelength and intensity. The manufacturing process, however, imposes certain restrictions on the product in terms of cost and the availability of only those dyes that are soluble in organic solvents.

Matech™ (Health Scientific Ltd., Buckinghamshire, UK) provide fluorescence reference standards ('FRS') in the form of multi-well plates. Many of the wells of these plates contain a series of inorganic standards, at varying concentrations, which are radioactive in nature and which emit fluorescent signals of specific wavelength and intensity when irradiated by a particular source. Due to the radioactive nature of the inorganic standard, it may be necessary to apply certain safety restrictions when handling or using these plates. Furthermore, the number of reference standards are restricted to those 'inorganic standards' commercially available.

There is therefore a need for a cost effective reference plate which can be used in either simple diode/PMT modality or multi-CCD-imaging modality to calibrate fluorescent instruments. The present invention addresses many of the above mentioned limitations of the prior art devices and provides a multi-modality fluorescence plate which can be used to calibrate plate alignment, fluorescence wavelength, intensity and lifetime.

SUMMARY OF THE INVENTION

According to the first aspect of the present invention, there is provided a multi-modality fluorescence reference plate comprising one or more wells, each well comprising a base, wherein the base of at least one well comprises a coating of a fluorogenic compound. The term 'well' is to be understood to mean a discrete area, defined by its base, which may be used to support a volume of a test sample. Thus, for example, the well may be two-dimensional in nature supporting a liquid sample on the surface of its base. Preferably, the well is three dimensional in nature and comprises one or more walls.

Preferably, the coating is applied by ink jet printing to the base. The advantages of ink jet printing over other marking methods are cost and precision as the process is relatively cheap yet extremely accurate. Thus a series of discrete particles containing the fluorogenic compound can be precisely printed onto the surface of the base to form a continuous coating thereon.

Suitably, the coating is applied by screen-printing to the base.

Suitably, the base comprises printing paper or card. Preferably, the printing paper or card comprises a metallic film. Typically, the metallic film is selected from the group consisting of aluminium, tin, silver and gold. Most preferably, the metallic film comprises aluminium.

Preferably, the printing paper or card further comprises a polymeric coating. More preferably, the polymeric coating comprises an organic polymer.

A suitable printing paper is, for example, 'Silver Glossy Film', available from Sensitisers Group Ltd. (Sensitisers International Ltd., Cornwall, UK), product reference number F102CMET.

Suitably, the base comprises an organic polymer. Preferably the polymer is selected from the group consisting of polyethylene, polystyrene, polyvinyl chloride (PVC) and nylon.

Suitably, the base comprises a metal. Preferably the metal comprises aluminium or stainless steel.

Suitably, the reference plate additionally comprises a support affixed to a second surface of the base. The support may, for example, comprise a rubber sheet. A bottom may be affixed to a second surface of the support. The bottom may comprise a solid sheet of a metal, plastic or paper material and may be secured to the support by an adhesive.

Suitably, the fluorogenic compound consists of stable, non-radioactive atoms. The use of non-radioactive atoms avoids any restrictions being placed upon the use of the plate in terms of operator safety, handling and transport.

Suitably, the fluorogenic compound comprises an unstable radioactive isotopic compound. Typical examples are isotopes which emit $\beta$-particles, such as 14C and 3H. The isotopes are applied in a scintillation fluid such as PPO or POPOP, which are well known in the art, or in the presence of a phosphor. Suitable phosphors are organic chelates of europium or inorganic host materials doped with europium as described in U.S. Pat. No. 6,524,786 and WO 99/09415. Aqueous soluble scintillant materials can also be used, such as those employed in commercial preparations (e.g. Amplify™ Fluorographic reagent, Amersham Biosciences) which are well known to those skilled in the art.

Preferably, the fluorogenic compound is selected from the group consisting of fluorescein, rhodamine, umbeliferone, Hoechst 33342, Cy2, Cy3, Cy3B, Cy5, Cy5B, Cy7, CypHer, coumarin, DAPI, Alexa dyes, DRAQ5, acridone, quinacridone, lanthanide chelate, ruthenium complexes, tartrazine, green fluorescent proteins (GFP), phycocyanin, allophycocyanin, and phycoerythrin. The acridone and quinacridone fluorogenic compounds are described in PCT Patent Applications GB02/02509 (WO 02/099424) and GB02/02537 (WO 02/099432), respectively. Typical lanthanide chelates include europium, terbium, samarium and dysprosium.

The fluorogenic compound is first dissolved or suspended in an aqueous or organic solvent and transferred to a standard ink jet printer cartridge for printing on to a base sheet.

Suitably, the number of wells in the plate is selected from the group consisting of one, six, twelve, twenty-four, forty-eight, ninety-six, three hundred and eighty-four and fifteen hundred and thirty-six. Preferably, the micro-well plate consists of ninety-six, three hundred and eighty-four or fifteen hundred and thirty-six wells.

It will be understood that the reference plates of the invention can be read from above by "top" reader systems, as herein before described, or inverted and read from below by "bottom" read instruments (e.g. Imagetrak/Zeiss readers).

In a second aspect of the present invention, there is provided the use of the reference plated as herein before described for calibrating instruments used for measuring steady-state fluorescence, time-resolved fluorescence, fluorescence lifetime and/or fluorescence polarisation. In this context, the term calibrating relates to the wavelength of the fluorescent signal, the intensity of the fluorescent signal, the lifetime or duration of the fluorescent signal, and/or the alignment of the microwell plate. It will be understood that calibration of instruments is required for a range of tasks, including instrument acceptance testing, quality control, instrument performance measurements and trouble shooting. Alignment can be checked by moving the plate, relative to the reader, into a position where the maximum fluorescent intensity is observed. It will further be understood that the reference plate of the invention can also be used for data normalisation, data correction and/or image correction.

Suitably, the instrument is selected from the group consisting of plate reader and imaging system. Suitable plate reader instruments included Envision™, (Perkin Elmer) and Farcyte™ (Amersham Biosciences). Preferably, the instrument is an imaging system. Most preferably, the instrument is a Leadseeker™ or Viewlux™ imaging system.

In a third aspect of the present invention, there is provided a method of producing a multi-modality fluorescence reference plate comprising the steps of:

i) ink jet printing or screen-printing a fluorogenic compound onto a first surface of a base sheet; and ii) affixing a base sheet to a first surface of a plate comprising one or more wells to provide a seal there between.

Preferably, the seal is a water-tight seal if liquids are to be dispensed into any wells in the plate.

Optionally, the method additionally comprises the subsequent step of securing a support to a second surface of the base sheet to provide strengthening therefor. Preferably, the support comprises two flat surfaces such that one flat surface abuts against the base sheet and the other provides a standing surface for the micro-well plate. Optionally, a bottom sheet may be secured to a second surface of the support to provide a standing surface for the reference plate.

Preferably, the base sheet comprises printing paper or card. Preferably, the printing paper or card comprises a metallic film selected from the group consisting of silver, aluminium, tin or gold. Most preferably, the metallic film comprises aluminium.

Preferably, the printing paper or card additionally comprises a polymeric coating. More preferably, the polymeric coating comprises an organic polymer.

Suitably, the base sheet comprises an organic polymer. Preferably the polymer is selected from the group consisting of polyethylene, polystyrene and polyvinyl chloride (PVC)

Suitably, the base comprises a metal. Preferably the metal comprises aluminium or stainless steel.

Suitably, the fluorogenic compound is first dissolved or suspended in an aqueous or organic solvent and transferred to a standard ink jet printer cartridge for printing on to a base sheet.

Suitably, the fluorogenic compound is selected from the group consisting of fluorescein, rhodamine, umbeliferone, Hoechst 33342, Cy2, Cy3, Cy3B, Cy5, Cy5B, Cy7, CypHer, coumarin, DAPI, Alexa dyes DRAQ5, acridone, quinacridone lanthanide chelates, ruthenium complexes, tartrazine, green fluorescent proteins (GFP), phycocyanin, allophycocyanin and phycoerythrin. Typical lanthanide chelates include europium and terbium, dysprosium and samarium.

Preferably, the fluorogenic compound consists of stable, non-radioactive atoms.

Suitably, the fluorogenic compound comprises an unstable radioactive isotopic compound. Typical examples are isotopes which emit β-particles, such as 14C and 3H. The isotopes are applied in a scintillation fluid such as PPO or POPOP, which are well known in the art, or in the presence of a phosphor. Suitable phosphors include organic chelates of europium or inorganic host materials doped with europium as described in U.S. Pat. No. 6,524,786 and WO 99/09415. Aqueous soluble scintillant materials can also be used, such as those employed in commercial preparations (e.g. Amplify™ Fluorographic reagent, Amersham Biosciences) which are well known to those skilled in the art.

Suitably, the number of wells in the plate is selected from the group consisting of one, six, twelve, twenty-four, forty-eight, ninety-six, three hundred and eighty-four and fifteen hundred and thirty-six. Preferably, the plate consists of ninety-six, three hundred and eighty-four or fifteen hundred and thirty-six wells.

BRIEF DESCRIPTION OF THE FIGURES

FIGS. 1a and 1b are schematic representations of ink jet printing a fluorogenic compound(s) onto the surface of a base sheet;

DETAILED DESCRIPTION OF THE PREFERRED EMBODIMENTS

Figure 2A:
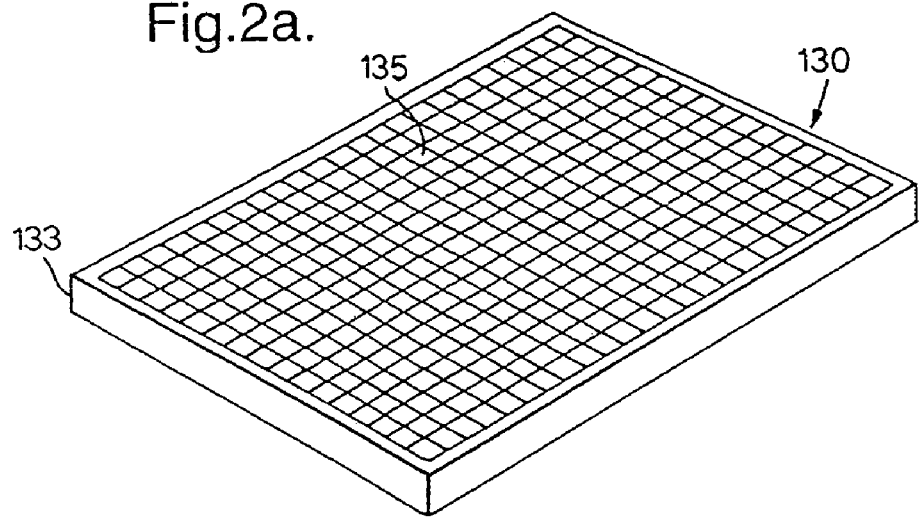
FIGS. 2a, 2b and 2c illustrate affixing a base sheet to a plate having a plurality of micro-wells within it.

FIGS. 1a and 1b schematically illustrate ink jet printing of a fluorogenic compound (or compounds) onto a first surface of a base sheet (10). In the example shown (FIG. 1a), the base sheet (10) is composed of printing paper which comprises an aluminium film (13) covering a first surface of paper (15). The aluminium film (13) may optionally be covered by a polymeric coating (not shown) to facilitate the subsequent printing process. Suitable printing paper is, for example, 'Silvery Glossy Film' (ref. F012CMET) from Sensitisers Group Ltd. The fluorogenic compound is dissolved in a suitable aqueous solvent and the resulting solution poured into a standard ink jet cartridge (e.g. Hewlett Packard (HP) 516410A or Canon BCI-21). In FIG. 1a, the solution containing the fluorogenic compound (22) is printed onto the surface of the aluminium film (13) from the ink jet printer nozzle (20). In other embodiments it will be understood that the base sheet (10) may be composed of a plastic polymer which can be directly printed upon.

FIG. 1b depicts a coating of fluorogenic compound (12), shown by the hatched lines, which has been printed over the surface of the aluminium film (13) of the base plate (10). It will be understood that the ink jet printing process can be carefully controlled to print on specific areas of the base plate (10); in this manner, only those regions of the plates which will be finally read by the fluorometer can be treated with the fluorogenic compound. For example, it is possible to control printing such that only the base of each well will be coated with the solution containing the fluorogenic material, thus saving material and time costs.

Ink jet printing of fluorogenic compounds is known in the art U.S. Pat. No. 6,402,986, for example, describes a method of ink jet printing an aqueous solution of a europium derivative, using a standard HP cartridge, to aid product identification and verification. US 2002/0047884 also describes the use of specific ink compositions containing mixtures of fluorescent compounds which can be applied to articles by ink jet printing. In both the above examples, however, the dyes are used in a qualitative rather than a quantitative manner to mark and identify products.

Figure 2B:
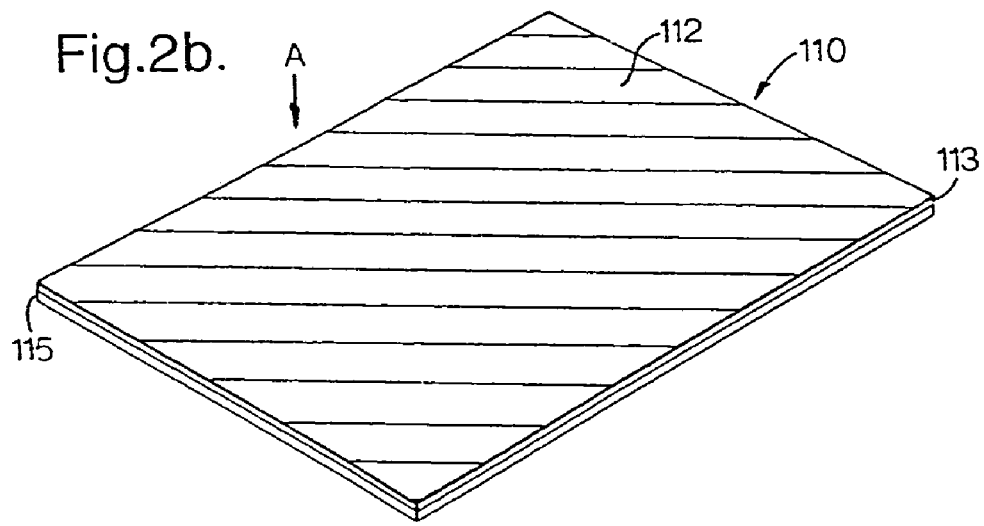
Figure 2C:
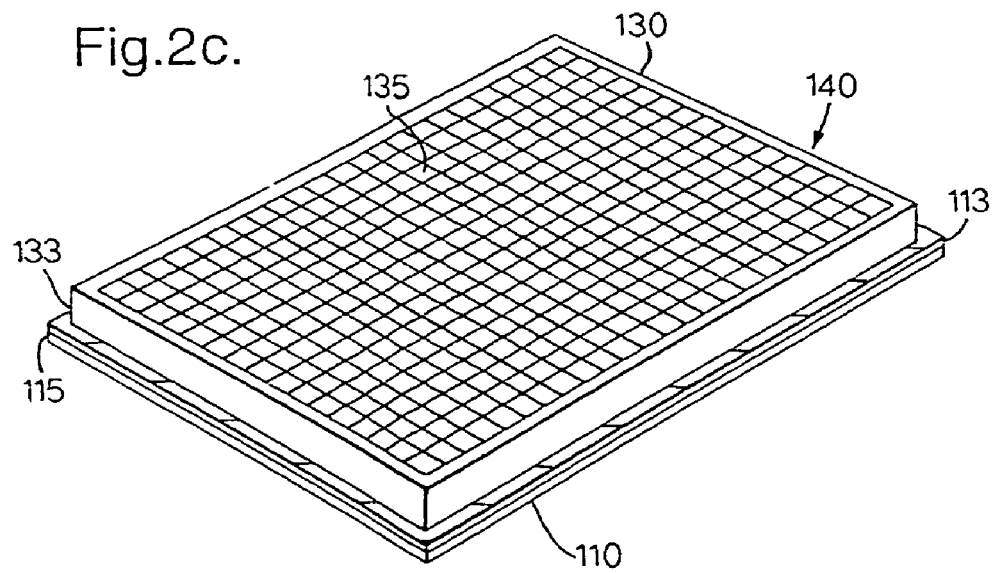

FIGS. 2a–c depict the process whereby the base sheet (110) is affixed to the plate (130). In FIG. 2a the plate (130) is shown to consist of a block, with sides (133), comprising a plurality of wells (135) running through it. In the example shown, there are 384 wells in the block, but other examples, such as 24, 48, 96 and 1536 are equally possible. Typically the block is composed of black polystyrene but other materials, including other plastics and metals (e.g. aluminium), can be used.

FIG. 2b shows the base sheet (110) of FIG. 1b, coated with the fluorogenic compound (112), in position to be affixed to the plate (130). The joining or affixing process (arrow A) can be achieved by methods well known in the art, such as adhesive or welding means, to secure a seal between the base sheet (110) and the plate (130). The seal achieved may be water-tight if the plate is to be used with liquid samples. Where the fluorogenic compound is only applied to specific areas of the base sheet, the accuracy with regards to the alignment of the plate and base sheet is obviously critical as the wells must be positioned only above those areas of the sheet which have a coating of fluorogenic material.

Once the base sheet (110) has been joined to the plate (130) by the affixing process (FIG. 2c), the micro-well plate (140) is ready for use. As can be seen, the base plate (110) is wider and longer than the plate (130) to ensure that a secure seal is achieved. It will, however, be understood that an acceptable seal will be obtained provided the base sheet is wider than the area of the wells (and not necessarily wider than the plate area). In such a situation, the base sheet fits within the 'footprint' of the micro-well plate (140) such that it is inset within the side walls (133). In some situations, where liquid assay solutions or samples are to be dispensed into the wells (135) of the plate (140), it will be essential that water-tight joins are obtained. Typical volumes of assay solutions will range between 1 µl and 1 ml.

Although not shown in FIGS. 2a–c it will be understood that an additional support can be placed adjacent to a second surface of the base sheet to provide strengthening.

Figure 3A:
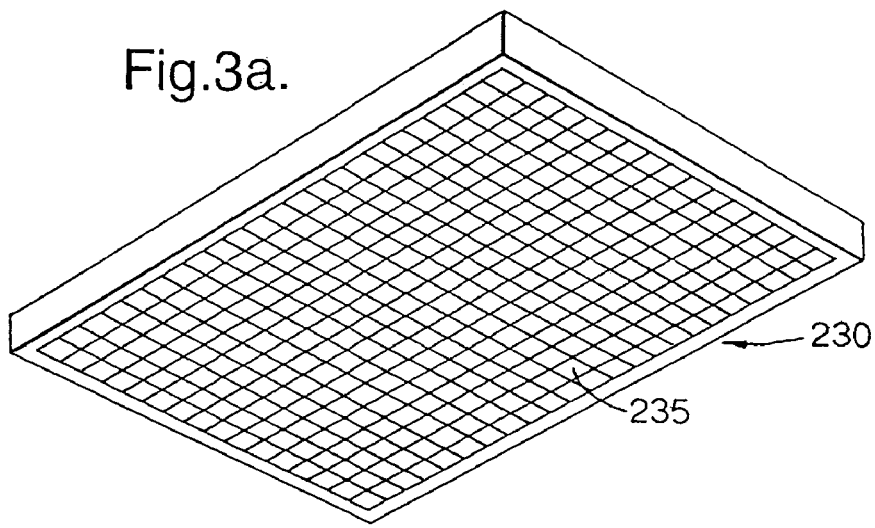
FIGS. 3a, 3b and 3c depict the same process as FIGS. 2a, 2b and 2c except that the base sheet is of lesser area.
Figure 3B:
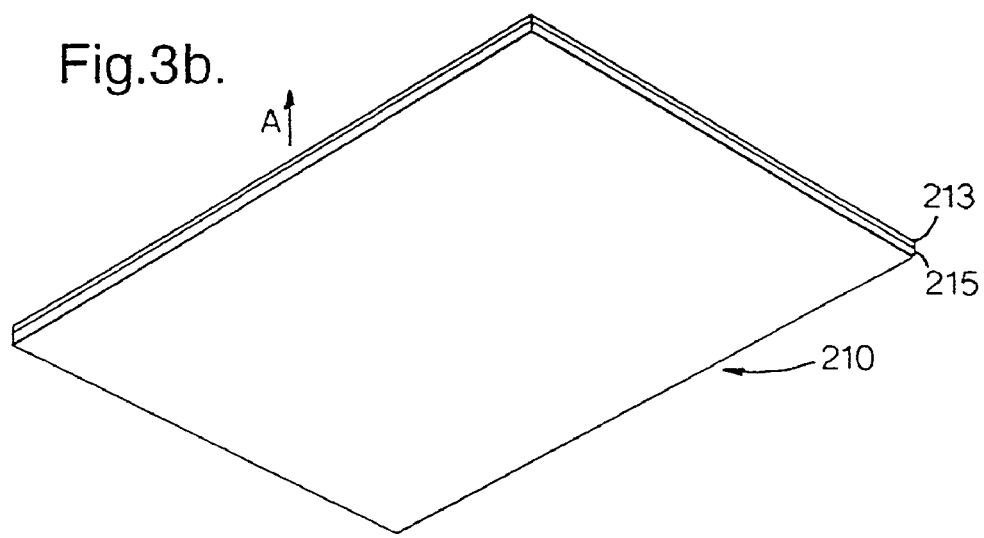
Figure 3C:
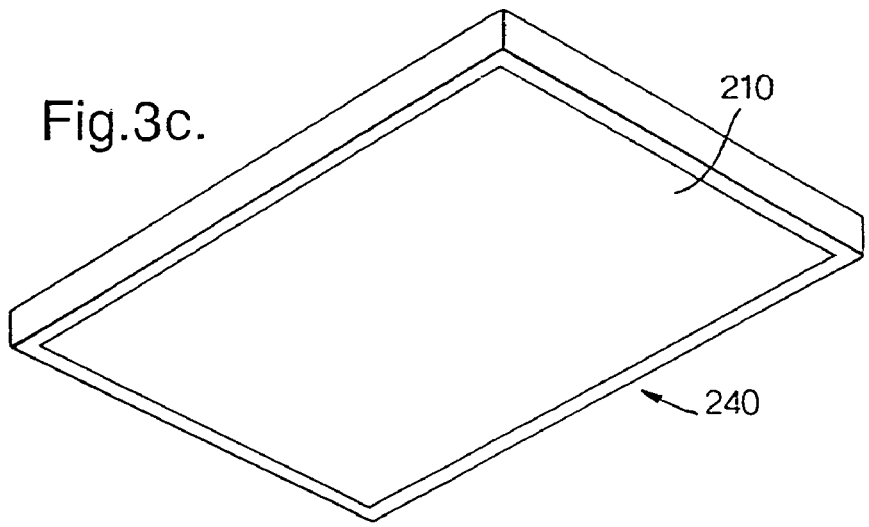

FIGS. 3a–c represent the affixing of a base sheet (210) to the plate (230) where the base sheet (210) is of only marginally greater area than the total area of the wells (235). FIG. 3a schematically illustrates a perspective underside plan view of the plate (230), shown to comprise a plurality of wells (235) running through it.

In FIG. 3b the base sheet (210) can be seen to comprise an aluminium film (213) on top of a paper sheet (215). The exposed surface of the aluminium film (213), which is not shown in the perspective view, has been coated with a fluorogenic compound (as described in FIG. 1 above). This coated surface is affixed or joined to the base of the plate (230), as shown by arrow A, to form a seal between the contacting surfaces. The affixing process can be achieved by any conventional means known in the art, such as welding or adhesion.

FIG. 3c depicts the resulting micro-well plate (240) in which the base sheet (210) has been joined to the plate (230) such that the fluorogenic-coated surface of the sheet now forms the base of the wells (not shown). As can be seen, the base sheet fits within the 'foot-print' of the micro-well plate (240) since the area of the base plate is only marginally greater than that of the wells in the plate.

Although not shown in FIGS. 3a–c, an additional supporting panel (for example, of polythene or rubber) may optionally be joined to the exposed and untreated surface of the base sheet (210) to strengthen it.

Figure 4A:
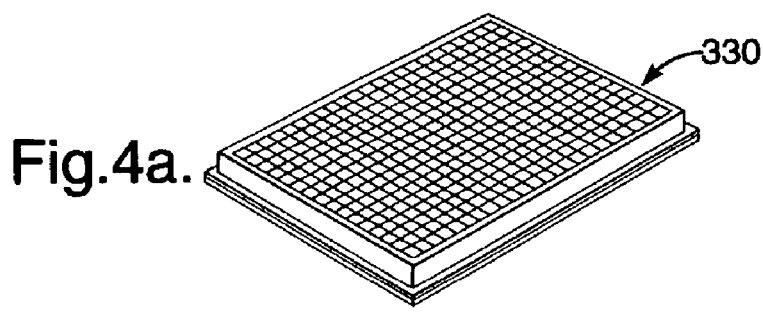
FIGS. 4a, 4b, 4c, 4d and 4e show an exploded view of the component parts of an embodiment of the invention.
Figure 4B:
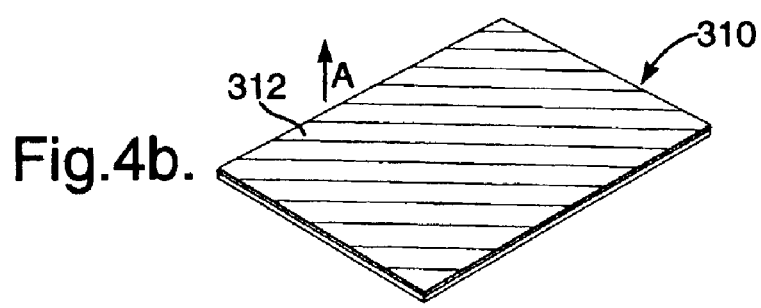
Figure 4C:
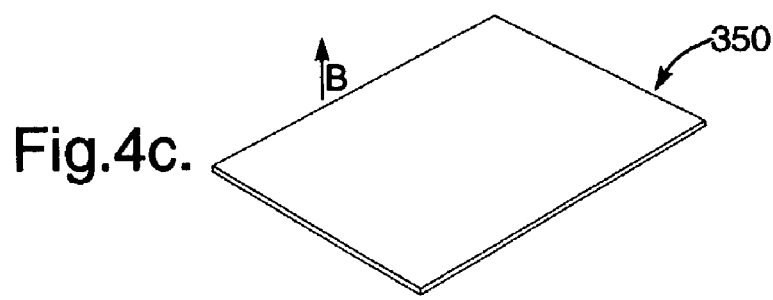
Figure 4D:
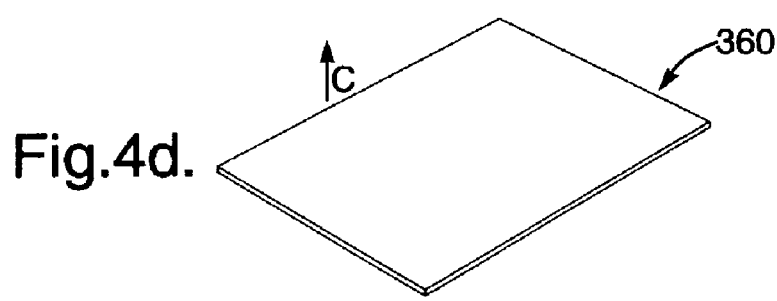
Figure 4E:
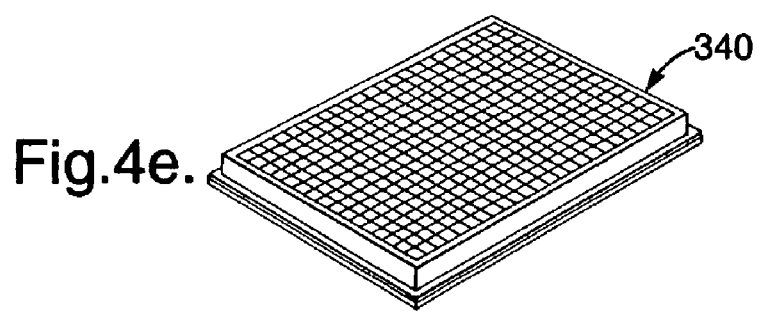
Figure 5A:
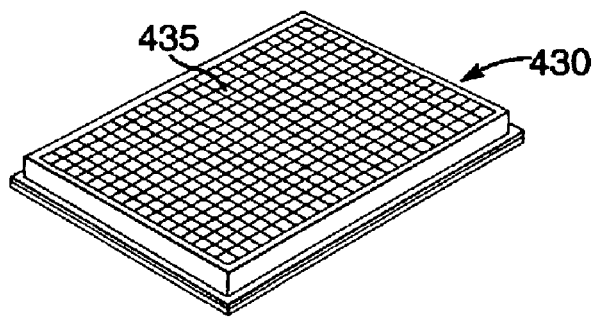
FIGS. 5a, 5b, 5c and 5d illustrate an exploded view of another embodiment of the invention which can be read from below.
Figure 5B:
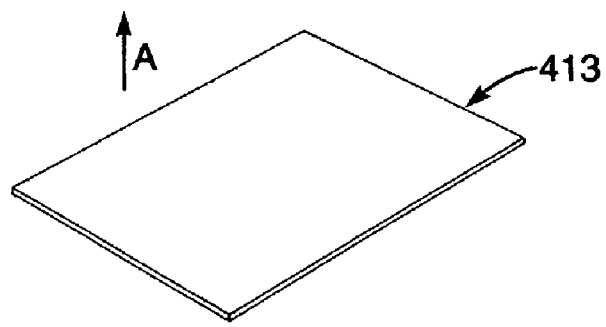
Figure 5C:
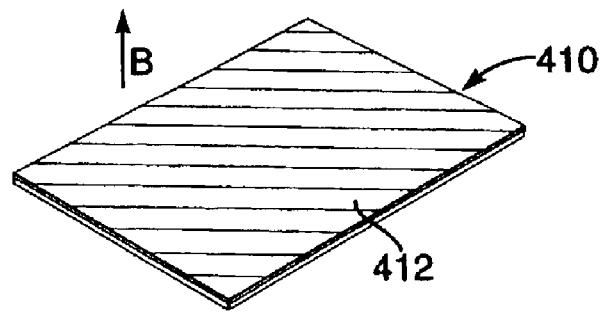
Figure 5D:
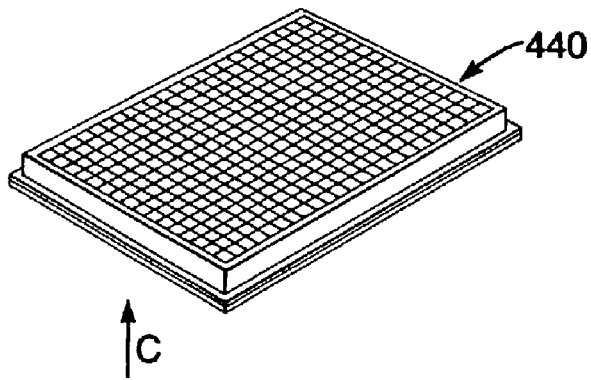

The exploded diagram of FIGS. 4a–e illustrates another embodiment of the present invention in which a rubber support (350) is inserted between the base sheet (310) and a metal bottom (360) sheet to secure the base sheet into position within the plate (330). Thus, the base sheet (310) of FIG. 4b, which has been coated with a fluorogenic compound (312), is initially positioned within the plate (330) of FIG. 4a by insertion from below as shown by Arrow A. The base sheet (310) is then locked into position by insertion of the support (350, FIG. 4c) and bottom sheet (360, FIG. 4d), as indicated by Arrows B & C. The bottom sheet (360) may be dimensioned to 'snap-fit' into position within the plate (330) or may be secured to the plate (330) and the support (350) by a suitable adhesive, such as glue. The resulting micro-well reference plate (340) is shown in FIG. 4e.

The exploded diagram of FIGS. 5a–d illustrates another embodiment of the present invention which can be used in the INCell™ 1000 and 3000 instruments and any other instruments of this type.

An unprinted sheet of foil (413) is attached to the base of the plate top (430), as shown by arrow A. A transparent base (410), for example an overhead transparency, which has been overprinted with a fluorogenic compound (either over its entire surface (as shown—412) or in the form of the requisite number of circles/squares matching the number and area of wells (435) in the plate top (430)), is joined to the foil (413) as shown by arrow B. The printing of the fluorogenic compound is on the top surface of the transparency beneath the foil. The resulting micro-well plate (440) is read from below as shown by arrow C.

Figure 6A:
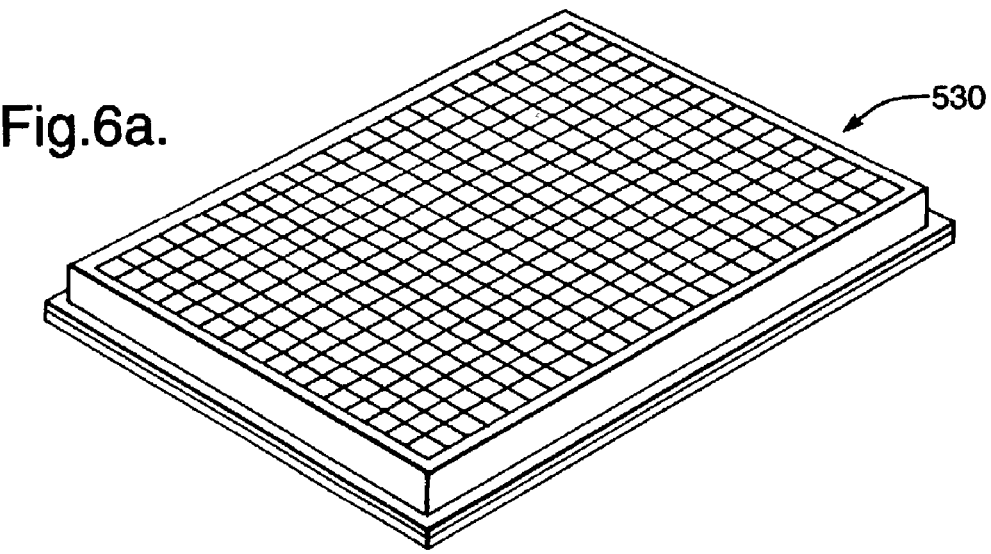
FIGS. 6a, 6b, and 6c depict an other 'bottom read' embodiment of the invention.
Figure 6B:
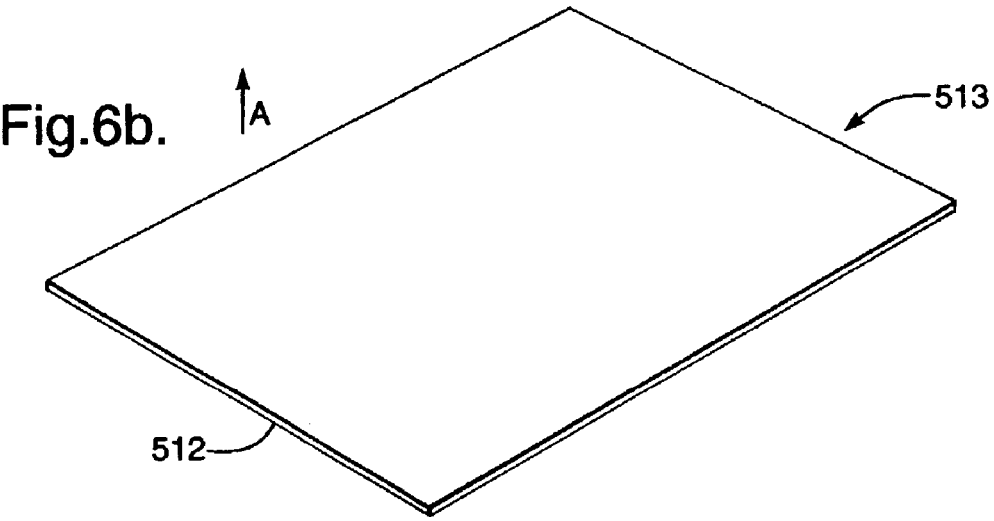
Figure 6C:
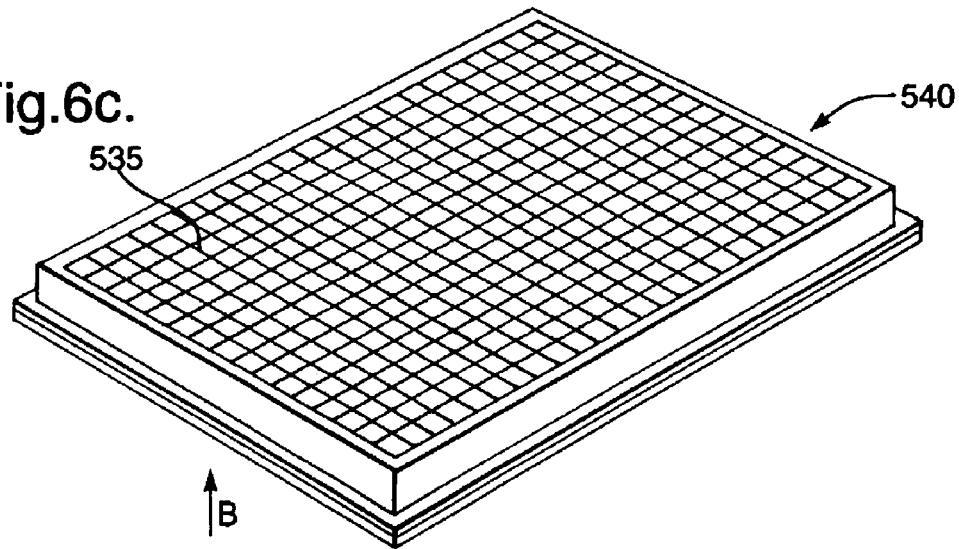

The exploded diagram of FIGS. 6a–c illustrates another embodiment of the present invention which can be used as a bottom read reference plate. The foil (513) is attached to the lower surface of the plate top (530 and Arrow A) and the bottom surface of the foil (not shown) is coated with a fluorogenic compound (512), either across its entire surface or by the number of spots corresponding to the number of wells (535) in the plate top (530). The resulting micro-well plate (540) can be read from underneath as shown by arrow B.

EXAMPLES

The following example are illustrative of certain preferred embodiments of the instant invention but are not intended to be illustrative of all embodiments.

Typical fluorescence results from a reference plate made according to the present invention are shown in Table 1. The fluor Cy3 was dissolved in an aqueous printing ink base (Coates Brothers plc, Bath, UK) to give a concentration of 10 µM. The solution was added to a Canon BCI-21 ink jet cartridge and inserted into a standard Canon S100 printer. A uniform coating of Cy3 was then applied to a base sheet, comprising 'Silver Glossy Film', by ink jet printing and a 384 well reference plate constructed as described in FIGS. 3a–c above.

Fluorescence intensity readings of all 384 wells were taken using an excitation wavelength of 558 nm with a Leadseeker™ imaging system. The average intensity is shown in Table 1 below. As can be seen, the coefficient of variation obtained is exceedingly low, highlighting the accuracy and precision of the printing process of the invention and the uniformity of the fluorescence signal achieved.

TABLE 1

Analysis of Fluorescence Measurements

| Description | Value |
| --- | --- |
| Number of Readings | 384 |
| Average Reading | 9538.1 (fluorescent intensity units) |
| Standard Deviation | 79.91927 (fluorescent intensity units) |
| Coefficient of Variation | 0.837895 |

Table 2 further illustrates typical data obtained from reference plates made according to the invention using the Leadseeker™ imaging system as described above. In this example, data were collected from plates coated with three different dyes—Cy3B, Europium Chelate and Cy2. Once again, the low coefficient of variation highlights the accuracy and precision of the printing process and the uniformity of the signal.

TABLE 2

Comparative Analysis of Fluorescence Measurements

| Dye | Cy3B | Europium Chelate | Cy2 |
|---|---|---|---|
| Average Reading | 24811.27 | 11932.4 | 50707.72 |
| Standard Deviation | 102.0601 | 88.87725 | 1601.339 |
| Coefficient of Variation | 0.411346 | 0.744839 | 3.157979 |

Representative data obtained using plate readers are shown in Table 3 using the Envision™ (Perkin Elmer) and Farcyte™ (Amersham Biosciences) systems and Cy3B dye. Results were obtained by generating standard protocols via the instrument software. Gain, focus height, etc. were generated by the instrument and associated software.

TABLE 3

Analysis of Fluorescence Measurements Using Plate Readers

| | Envision ™ | Farcyte |
|---|---|---|
| Average Reading | 7912305 | 38219.57 |
| Standard Deviation | 166929.8 | 949.9077 |
| Coefficient of Variation | 2.10975 | 2.485396 |

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A method of producing a multi-modality fluorescence reference plate comprising the steps of:
    i) ink jet printing or screen-printing a fluorogenic compound onto a first surface of a base sheet; and
    ii) affixing said base sheet to a first surface of a plate comprising one or more wells to provide a seal therebetween.

2. The method of claim 1, wherein said seal is a water-tight seal.

3. The method of claim 1, wherein the base sheet includes printing paper or card.

4. The method of claim 3, wherein said printing paper or card includes a metallic film.

5. The method of claim 4, wherein said metallic film is selected from the group consisting of silver, aluminium, tin and gold.

6. The method of claim 1, wherein the printing paper or the card further comprises a polymeric coating.

7. The method of claim 1, wherein the base sheet includes an organic polymer.

8. The method of claim 7, wherein said organic polymer is selected from the group consisting of polyethylene, polystyrene polyvinyl chloride, polyvinyl alcohol (PVA) and nylon.

9. The method of claim 1, wherein the base sheet includes a metal.

10. The method of claim 9, wherein said metal is aluminium or stainless steel.

11. The method of claim 1, further comprising the step of securing a first surface of a support to a second surface of the base sheet to provide strengthening therefor.

12. The method of claim 11, further comprising the step of securing a bottom to a second surface of said support.

13. The method of claim 1, wherein the fluorogenic compound is selected from the group consisting of fluorescein, rhodamine, umbeliferone, Hoechst 33342, Cy2, Cy3, Cy3B, Cy5, Cy5B, Cy7, CypHer, coumarin, FITC, DAPI, Alexa dyes, DRAQ5, acridone, quinacridone, lanthanide chelates, ruthenium complexes, tartrazine, green fluorescent proteins (GFP), phycocyanin, allophycocyanin and phycoerythrin.

14. The method of claim 1, wherein the fluorogenic compound consists of stable, non-radioactive atoms.

15. The method of claim 1, wherein the fluorogenic compound comprises an unstable, radioactive isotope.

16. The method of claim 1, wherein the number of wells in the plate is selected from the group consisting of one, six, twelve, twenty-four, forty-eight, ninety-six, three hundred and eighty-four, and fifteen hundred and thirty-six.

* * * * *